United States Patent
Wood

(10) Patent No.: US 12,417,538 B2
(45) Date of Patent: Sep. 16, 2025

(54) VALIDATION METHODS FOR MULTIPLEXED IMAGING METHOD

(71) Applicant: Ultivue, Inc., Cambridge, MA (US)

(72) Inventor: Douglas Wood, Hingham, MA (US)

(73) Assignee: Ultivue, Inc., Cambridge, MA (US)

( * ) Notice: Subject to any disclaimer, the term of this patent is extended or adjusted under 35 U.S.C. 154(b) by 46 days.

(21) Appl. No.: 18/435,336

(22) Filed: Feb. 7, 2024

(65) Prior Publication Data

US 2024/0242353 A1     Jul. 18, 2024

Related U.S. Application Data

(62) Division of application No. 16/213,391, filed on Dec. 7, 2018, now Pat. No. 11,935,240.

(60) Provisional application No. 62/630,405, filed on Feb. 14, 2018, provisional application No. 62/596,587, filed on Dec. 8, 2017.

(51) Int. Cl.
| | |
|---|---|
| *G06T 7/00* | (2017.01) |
| *C12Q 1/6804* | (2018.01) |
| *G01N 21/64* | (2006.01) |
| *G01N 33/569* | (2006.01) |
| *G06T 3/14* | (2024.01) |

(52) U.S. Cl.
CPC ........... *G06T 7/0014* (2013.01); *G01N 21/64* (2013.01); *G01N 21/6458* (2013.01); *G01N 33/56966* (2013.01); *G06T 3/14* (2024.01); *C12Q 1/6804* (2013.01); *G01N 2333/7051* (2013.01); *G01N 2458/10* (2013.01); *G06T 2207/10056* (2013.01); *G06T 2207/10064* (2013.01); *G06T 2207/10081* (2013.01); *G06T 2207/30024* (2013.01)

(58) Field of Classification Search
CPC .. C12Q 1/6804; G01N 21/64; G01N 21/6458; G01N 33/554; G01N 33/56966; G01N 2458/10; G06T 3/14; G06T 7/0014; G06T 2207/10056; G06T 2207/10064; G06T 2207/10081; G06T 2207/30024
See application file for complete search history.

(56) References Cited

U.S. PATENT DOCUMENTS

| | | | |
|---|---|---|---|
| 11,935,240 B2 * | 3/2024 | Wood | G06T 7/0014 |
| 2016/0319328 A1 | 11/2016 | Yin et al. | |
| 2018/0164308 A1 | 6/2018 | Walter et al. | |

OTHER PUBLICATIONS

Bacia et al., "Correcting for Spectral Cross-Talk in Dual-Color Fluorescence Cross-Correlation Spectroscopy," ChemPhysChem 13(5):1221-1231 (2012).
Bay et al., "SURF: Speeded Up Robust Features," Science Direct Computer Vision and Image Understanding 110, pp. 346-359 (2008).
Giesen et al., "Highly multiplexed imaging of tumor tissues with subcellular resolution by mass cytometry," Nature Methods, vol. 11, No. 4, pp. 417-425 (2014).

(Continued)

*Primary Examiner* — Robert J Eom
(74) *Attorney, Agent, or Firm* — Anderson IP; Koren Anderson

(57) ABSTRACT

A quantitative method of validating at least one candidate imaging method or candidate imaging reagent for use in evaluating a biological sample for the presence of one or more targets is described relying upon cross-correlation calculations.

47 Claims, 7 Drawing Sheets
(3 of 7 Drawing Sheet(s) Filed in Color)

(56) References Cited

OTHER PUBLICATIONS

Krieger, et al. "Imaging fluorescence (cross-) correlation spectroscopy in live cells and organisms." Nature protocols 10.12:1948-1974 (2015).
Lowe, David G., "Distinctive Image Features from Scale-Invariant Keypoints," International Journal of Computer Vision, pp. 1-28 (2004).
Norris et al., Imaging Mass Spectrometry: A New Tool for Pathology in a Molecular Age, Proteomics Clin. Appl., pp. 1-9 (2013).
Parra et al, "Validation of multiplex immunofluorescence panels using multispectral microscopy for immune-profiling of formalin-fixed and paraffin-embedded human tumor issues," Scientific Reports, pp. 1-16 (2017).
Singh et al., "Fixation and Fixatives: Roles and Functions—A Short Review," Dental Journal of Advance Studies, vol. 07, No. 2/2019, pp. 51-55.
Welch et al., "Imaging the coordination of multiple signaling activities in living cells," Nature Reviews Molecular Cell Biology 12(11):749-756 (2011).

\* cited by examiner

FIG. 6A
FIG. 6B
Zone A
In Fluorescent Image 1
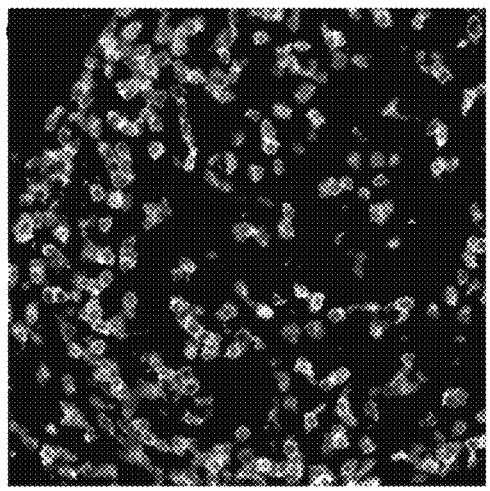
In Chromogenic Image 2
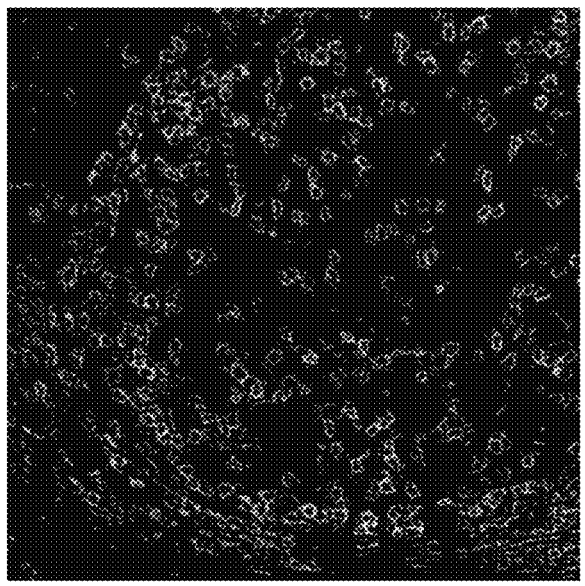
FIG. 6C
FIG. 6D
Zone B
In Fluorescent Image 1
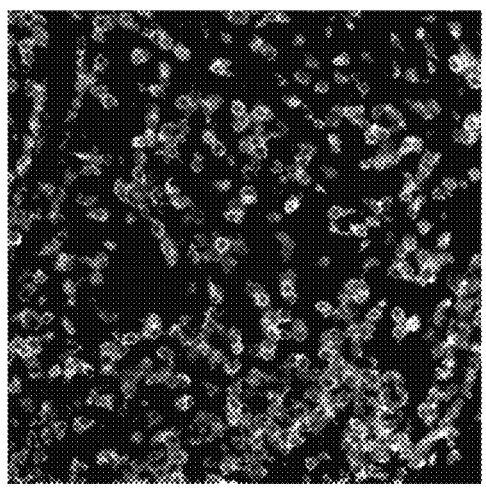
In Chromogenic Image 2
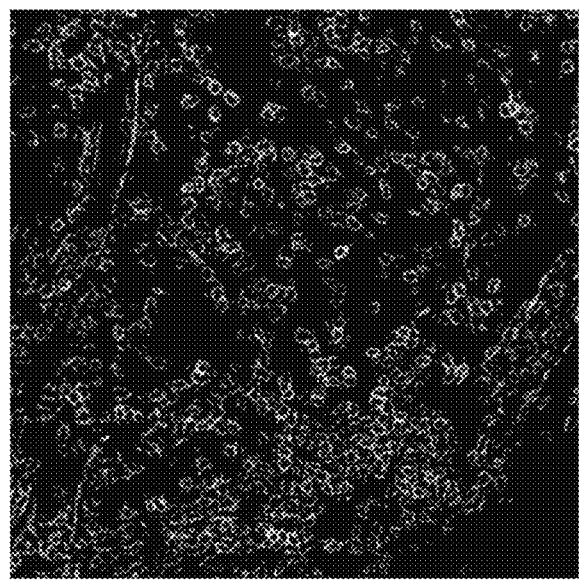

A vs. A

B vs. B

A vs. B

B vs. A

VALIDATION METHODS FOR MULTIPLEXED IMAGING METHOD

CROSS-REFERENCE TO RELATED APPLICATIONS

This application is a division of U.S. application Ser. No. 16/213,391, filed Dec. 7, 2018, which claims the benefit of priority of US Provisional Application Nos. 62/596,587, filed Dec. 8, 2017, and 62/630,405, filed Feb. 14, 2018, the contents of all of which are incorporated by reference herein in their entirety for any purpose.

FIELD

This application relates generally to the field of detection and quantification of analytes (e.g., targets) and the comparison of different imaging reagents and methods.

BACKGROUND

Imaging of biological samples is useful in the diagnosis, treatment, and management of many diseases, including, for example, cancer. Common imaging methods include fluorescence microscopy, brightfield microscopy, electron microscopy and mass spectrometry imaging. Not every imaging method suits each situation and investigators can be required to switch between imaging methods. It is useful to determine the degree of similarity between results of different imaging methods. When a new method is reasonably comparable to an accepted method, it is often said to be validated against the accepted method. Additionally, investigators often desire to validate new reagents for use in imaging methods.

The present application describes a method for comparing imaging methods and reagents that is quantitative, capable of automation, streamlined, and, in some embodiments, does not require multiple staining steps that could alter the conditions of the biological sample and reduce the effectiveness of the comparison.

SUMMARY

In accordance with the description, a quantitative method of validating at least one candidate imaging method or candidate imaging reagent for use in evaluating a biological sample for the presence of one or more targets comprises:
  a. obtaining a first imaging signal using a first imaging method and/or first imaging reagents comprising:
     i. contacting a biological sample with one or more target-specific binding partners, wherein each target-specific binding partner is linked to a nucleic acid strand and wherein target-specific binding partners of different specificity, if present, are linked to different nucleic acid strands, wherein the nucleic acid strand is either a docking strand or a primer strand for amplification of docking strands;
     ii. contacting the biological sample with labeled imager strands for a first imaging method, wherein the labeled imager strands are capable of binding a docking strand, directly or indirectly,
     iii. generating a first imaging signal;
  b. optionally removing the bound labeled imager strands from the docking strands;
  c. obtaining a second imaging signal using a second imaging method and/or second imaging reagents comprising contacting the biological sample with either (1) labeled imager strands, wherein the labeled imager strands are capable of binding a docking strand, directly or indirectly, or (2) a secondary binding partner for the target-specific binding partner, wherein the second imaging method and/or the second imaging reagent is different than the first imaging method and/or first imaging reagent;
  d. optionally aligning the first imaging signal and the second imaging signal to adjust for signal orientation, image parity, scale, rotation, and/or translation mismatch,
  e. identifying a first imaging zone in both the first imaging signal and second imaging signal, wherein the first imaging zone in both imaging signals represents the same location in the biological sample;
  f. comparing the first imaging zone in the first imaging signal and the first imaging zone in the second imaging signal by performing a cross-correlation.

In some embodiments, a quantitative method of validating at least one candidate imaging method or candidate imaging reagent for use in evaluating a biological sample for the presence of one or more targets comprises:
  a. obtaining a first imaging signal using a first imaging method and/or first imaging reagents,
  b. obtaining a second imaging signal using a second imaging method and/or second imaging reagents,
     wherein the second imaging method and/or the second imaging reagent is different the first imaging method and/or first imaging reagent;
  c. optionally aligning the first imaging signal and the second imaging signal to adjust for signal orientation, image parity, scale, rotation, and/or translation mismatch,
  d. identifying a first imaging zone in both the first imaging signal and second imaging signal, wherein the first imaging zone in both imaging signals represents the same location in the biological sample;
  e. comparing the first imaging zone in the first imaging signal and the first imaging zone in the second imaging signal by performing a cross-correlation.

Additional objects and advantages will be set forth in part in the description which follows, and in part will be obvious from the description, or can be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, explain the principles described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 6A-D show the details of imaging zones A and B from the first imaging signal (Image 1) and the second imaging signal (Image 2).

DESCRIPTION OF THE EMBODIMENTS

Figure 1:
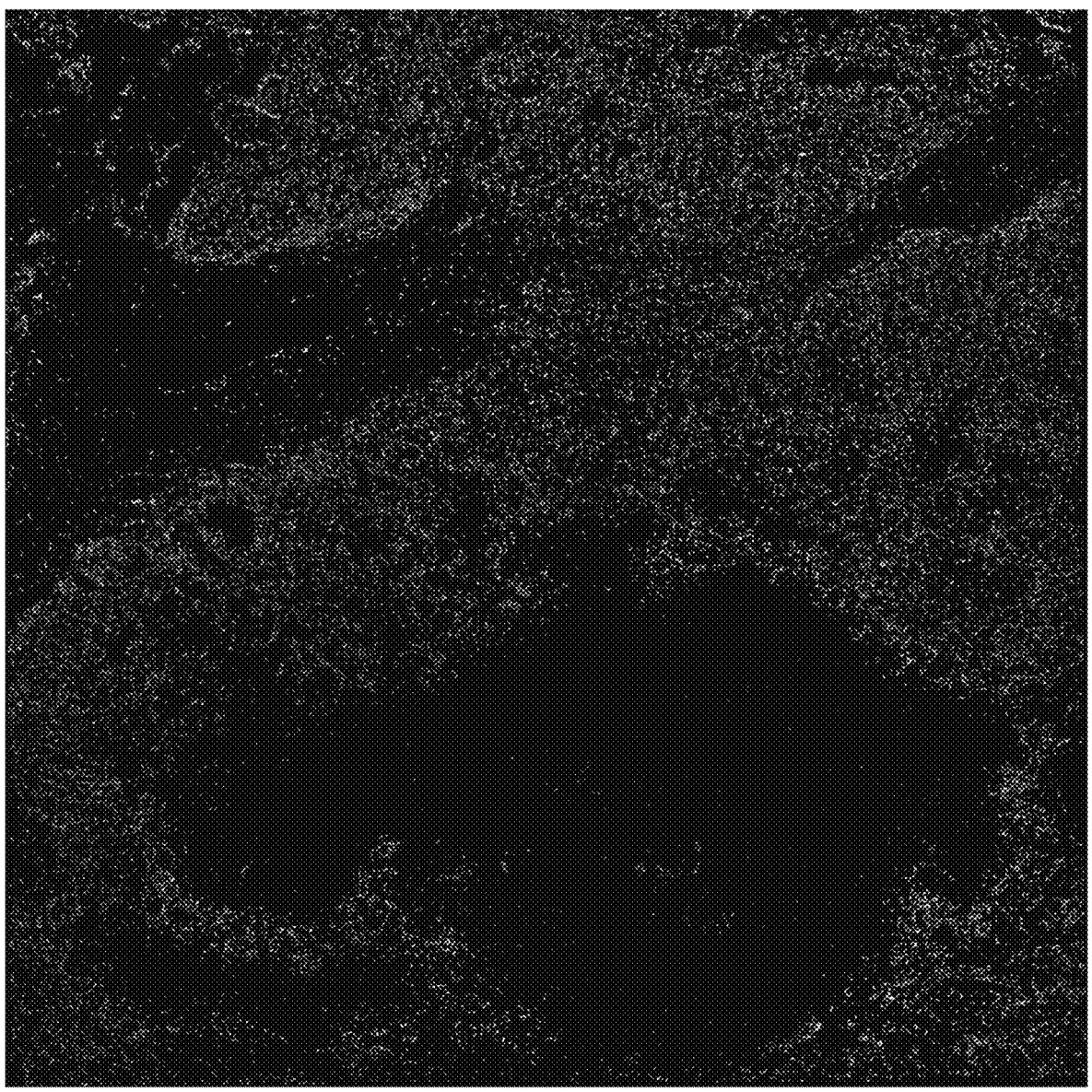
FIG. 1 provides a first imaging signal from a fluorescent stain of a biological sample.

I. Quantitative Methods for Validating Candidate Imaging Methods or Candidate Imaging Reagents The present application describes a quantitative method for comparing one or more candidate imaging methods or one or more candidate imaging reagents. The comparisons between methods can be made in a way that relies on computer processing to account for differences in the way different imaging methods report data or the view of any given instrument. Thus, this provides a robust and reliable way to evaluate different reagents and methods.

A quantitative method of validating at least one candidate imaging method or candidate imaging reagent for use in evaluating a biological sample for the presence of one or more targets comprises:
  a. obtaining a first imaging signal using a first imaging method and/or first imaging reagents comprising:
     i. contacting a biological sample with one or more target-specific binding partners, wherein each target-specific binding partner is linked to a nucleic acid strand and wherein target-specific binding partners of different specificity, if present, are linked to different nucleic acid strands, wherein the nucleic acid strand is either a docking strand or a primer strand for amplification of docking strands;
     ii. contacting the biological sample with labeled imager strands for a first imaging method, wherein the labeled imager strands are capable of binding a docking strand, directly or indirectly,
     iii. generating a first imaging signal;
  b. optionally removing the bound labeled imager strands from the docking strands;
  c. obtaining a second imaging signal using a second imaging method and/or second imaging reagents comprising contacting the biological sample with either (1) labeled imager strands, wherein the labeled imager strands are capable of binding a docking strand, directly or indirectly, or (2) a secondary binding partner for the target-specific binding partner wherein the second imaging method and/or the second imaging reagent is different the first imaging method and/or first imaging reagent;
  d. optionally aligning the first imaging signal and the second imaging signal to adjust for signal orientation, image parity, scale, rotation, and/or translation mismatch,
  e. identifying a first imaging zone in both the first imaging signal and second imaging signal, wherein the first imaging zone in both imaging signals represents the same location in the biological sample;
  f. comparing the first imaging zone in the first imaging signal and the first imaging zone in the second imaging signal by performing a cross-correlation.

In some embodiments, the quantitative method does not employ a target-specific binding partner linked to a nucleic acid strand or a labeled imager strand, but instead employs a target-specific binding partner that is not linked to a nucleic acid strand. Thus, a quantitative method of validating at least one candidate imaging method or candidate imaging reagent for use in evaluating a biological sample for the presence of one or more targets comprises:
  a. obtaining a first imaging signal using a first imaging method and/or first imaging reagents,
  b. obtaining a second imaging signal using a second imaging method and/or second imaging reagents, wherein the second imaging method and/or the second imaging reagent is different the first imaging method and/or first imaging reagent;
  c. optionally aligning the first imaging signal and the second imaging signal to adjust for signal orientation, image parity, scale, rotation, and/or translation mismatch,
  d. identifying a first imaging zone in both the first imaging signal and second imaging signal, wherein the first imaging zone in both imaging signals represents the same location in the biological sample;
  e. comparing the first imaging zone in the first imaging signal and the first imaging zone in the second imaging signal by performing a cross-correlation.

In such an embodiment, the first imaging method can employ a first targeting antibody bound directly or indirectly to a first label and the second imaging method can employ a second targeting antibody bound directly or indirectly to a second label. In some embodiments, one or both targeting antibodies are bound directly to their respective label.

The first imaging signal and the second imaging signal are from the same microscope slide and include at least some overlapping areas from the same microscope slide. In some embodiments, the areas are entirely overlapping and in other embodiments they are not entirely overlapping.

In some embodiments, cross-correlation comprises generating numerical data. In some embodiments, cross-correlation comprises generating an image representing the numerical data.

The cross-correlation can comprise identifying the peak cross-correlation between the first imaging zone in the first imaging signal and the first imaging zone in the second imaging signal. The cross-correlation can also comprise evaluating the breadth of the peak cross-correlation. The cross-correlation can, in some embodiments, comprise identifying and comparing secondary peaks and/or measuring the background of the cross-correlation.

The method can be used to compare two candidate imaging methods. The method can be used to compare two candidate imaging reagents. In some embodiments, the method can be used to compare more than two candidate imaging methods. In some embodiments, the method can be used to compare more than two candidate imaging reagents.

For example, the method can be used to compare 3, 4, 5, 6, 7, 8, 9, 10 or more candidate imaging methods or candidate imaging reagents.

Multiple candidate imaging methods or candidate imaging reagents can be compared by evaluating each candidate imaging method or candidate imaging reagent to a control (a previously used candidate imaging method or candidate imaging reagent) and/or by comparing each candidate imaging method or candidate imaging reagent to at least one other (one, some, or all) candidate imaging method or candidate imaging reagent.

A. Aligning the First Imaging Signal and the Second Imaging Signal

When the first imaging signal and the second imaging signal are generated using different modalities (for example, fluorescence imaging and brightfield imaging) or even when the first imaging signal and the second imaging signal are generated using different pieces of equipment, or when a sample is removed for further processing and reloaded, the user may need to align the first imaging signal and the second imaging signal before validation can take place. When the first imaging signal and the second imaging signal are generated using the same modality (for example, all fluorescent imaging) and/or optionally when they are generated using the same instrument and/or optionally when the sample is not removed and replaced from the field of view, it might not be necessary to perform any steps of aligning the first imaging signal and the second imaging signal. Additionally, when different modalities are used, different instruments are used, or when an operator removes and replaces the sample, the properties of the first imaging signal and the second imaging signal dictate which alignment steps should occur.

Through this process, either the first imaging signal is aligned to the second imaging signal or the second imaging signal is aligned to the first imaging signal (i.e., the alignment can be performed in either direction). The user can select the directionality of the alignment based on how many images are obtained from a given modality or instrument or depending on which type of alignment is more convenient for the user. For example, it can be more convenient to align a colored image to make it monochromatic but the image alignment steps can be performed in either direction (first signal to second signal or vice versa) and in any order. Additionally, it may be possible to align some aspects of the first signal to the second signal (for example changing the first signal, a colored image, to align to the monochromatic second signal), while aligning other aspects of the second signal to the first signal (for example to correct the image parity of the second signal to match the first signal).

The alignment steps described below could be undertaken in any order from the order presented here. For example, the steps for correcting for scale and rotation could be taken first and converting color spaces and matching for signal orientation could follow, but this might require additional computations (e.g. rotating a color image rather than a monochromatic one) or additional complexity (e.g. rotating backwards because one image has the opposite parity of the other). Similarly, it would also be possible to perform the alignment after selecting imaging zones for validation instead of the order presented here, but that order might require additional complexity in the identification of matching regions seen in unaligned images.

1. Signal Orientation and Color Spaces

Various forms of imaging produce signals with different meaning, referred to herein as orientation, to the value of the digital signal measured by the image detector. For example, in brightfield imaging, the background (no signal) is white (high data value) and when the signal is present, the image is darker (low data value). In fluorescence imaging, on the other hand, the background is dark (low data value), and regions with signal are bright (high data value). If two images have opposite orientations, their orientations can be aligned by inverting the orientation of one to match the other.

To adjust the orientation of an image, the maximum signal in the image (or the maximum possible data value produced by the detector) is determined; and all the pixel values are replaced in the image with the maximum minus the measured value. While it is possible to compare images with opposite orientations, one would either (1) need to instead look for an anti-correlation, rather than a correlation of the data values (e.g., matching a negative image to a positive one), or (2) need to change the calculation or the correlation to invert one of the sets of pixel values.

In addition, some imaging modalities, for example bright field imaging of a chromogenic stain, typically produce a multichannel (e.g., RGB) color image. Other modalities, for example fluorescence emission detected using interference filters tuned to transmit only a specific range of wavelengths, produce a monochromatic (single channel) image. Furthermore, in chromogenic imaging a stain of a particular color that indicates the presence of a signal of interest is examined and other colors in the stained image are treated as unwanted signals or background. Therefore, it is usually necessary to process the color image to produce a monochromatic (single channel) image that selects the signal or color of interest.

To align a color image to a monochromatic one, the RGB (Red, Green, Blue) pixel values are converted to HSV (Hue, Saturation, Value) space (using standard conversions), a range of hue values for the desired chromogenic stain color (e.g., brown=H~30±10°) is specified by the user, and a mask image of the pixels in this hue range is created. A mask image, as used herein, means an intermediate image used to identify pixels with the signal of interest. The mask image has values at each pixel generated by comparing the values in the initial image to a preset range and assigning one value in the mask image when the value in the initial image is within the preset range and another value when the value in the initial image is outside of the preset range.

Thus, in embodiments when a binary mask is made, the resulting mask image is 1 where ever the hue is in this range, and 0 elsewhere. Other embodiments could create a mask with a real number weight or probability value at each pixel location ranging from 0.0 to 1.0 indicating the likelihood that the given pixel represents a signal of interest. Finally, the Value channel of the HSV image is adjusted for orientation as described above and multiplied by the mask image to produce a monochromatic version of the initial color image. Thus, when the mask has a value of 0 the monochromatic version will also have a value of 0 and when the mask has a value of 1 the monochromatic version will have the value of the orientation adjusted Value channel of the HSV image.

a) Additional Adjustments

If desired, to improve the conversion of a colored image to a monochromatic image, one or more additional steps can be applied at different points in the adjustment or conversion process.

The method of adjusting the image(s) can also optionally include performing morphology operations common in image processing (see en.wikipedia.org/wiki/Mathematical_morphology) on the mask image used to select pixels which have the desired range of hue values to convert a chromogenic image to a monochrome image for a given stain color. Such operations can be used to eliminate very small features, to fill holes, smooth edges, etc. Such techniques are known to the person of ordinary skill in the art.

An intensity scaling step can optionally be performed for the monochromatic image. If this step is chosen by the user, the output can be scaled such that the smallest value in the mask region is zero and the largest value is 255 (or whatever is the maximum possible value) in the output. This scaling can be optionally included to improve the brightness and contrast of the image in later visualizations.

Although the methods are described herein with respect to HSV, other color spaces (e.g., HSL, Hue Saturation Lightness) can be used. Alternatively, the color image can be converted to luminance (a linear combination of the RGB value of each pixel that produces a grayscale from the color image), or a single channel could be selected (e.g., select the blue channel for a blue colored stain).

2. Image Parity

Some instruments image samples from the top, while other instruments image samples from the bottom of the slide, and/or some instruments contain optical elements (e.g., lenses or mirrors) that create a left-right or top-bottom reversal of the captured image. These differences in instrumentation can create parity misalignment between images captured with different instruments. Image parity refers to potential left-right reversal (reversion) and/or top-bottom reversal (inversion) of the images.

If an image has left-right parity reversal with respect to another, one image can be reflected about its vertical axis, by reversing the order of the pixel values in each row. If an image has top-bottom parity reversal with respect to the other, one image can be reflected about the horizontal axis, by reversing the order of rows top to bottom.

3. Image Scale, Rotation, and Translation Mismatch

Differences in the optics of two imaging systems and/or the act of positioning the biological sample on each instrument, can result in differences in the scale, rotation, and/or translation (x,y displacement) of the images captured on each device. Image scale refers to the pixel size in an image (i.e., how zoomed-in or zoomed-out an image appears). Image rotation refers to whether the image is rotated on the plane of imaging by any number of degrees. And image translation mismatch refers to whether the image is shifted up/down or left/right in the field of view between the first imaging signal and the second imaging signal.

There are a variety of ways to match the geometry of one image to another as this is a common problem in microscopy, computer vision and pattern recognition. One method is to first identify one or more (x,y) points in one of the images that match the same features of the sample as seen in another image and then adjust the scale, rotation and translation of one image so the points of one image match the other. The matching points can be identified using any method, including visual analysis and an automatically technique such as SURF (Speeded-Up Robust Features) (Bay, H., et al., "SURF: Speeded Up Robust Features," Computer Vision and Image Understanding 110:346-359 (2008)), or SIFT (Scale-Invariant Feature Transform) (D. Lowe, "Distinctive Image Features from Scale-Invariant Keypoints" International J. of Computer Vision 60:91 (2004)).

To align the geometry of one image to that of the other image, an Affine transformation of the form is performed $$\begin{bmatrix} a_{00} & a_{01} & b_{00} \\ a_{10} & a_{11} & b_{10} \\ 0 & 0 & 1 \end{bmatrix} \begin{bmatrix} x \\ y \\ 1 \end{bmatrix} = \begin{bmatrix} x' \\ y' \\ 1 \end{bmatrix}.$$

where (x, y) and (x', y') are the original and transformed coordinates respectively, and the matrix elements $a_{ij}$ and $b_{ij}$ are calculated from the collection of matching points. For example, for a translation offset, only one pair of matching points is required and the differences in the x and y coordinates of the points are $b_{00}$ and $b_{10}$ respectively. From three pairs of points, all the elements of the Affine transform can be calculated directly using linear algebra. For more than three points, the method of least squares or other parameter estimation techniques can be used.

In some embodiments, matching point pairs alone are used to calculate the complete Affine transform to align the geometry of the images. In some embodiments, matching point pairs are used to calculate the $a_{ij}$ matrix elements, the image is corrected for scale and/or rotation, and then the method of cross-correlation (described below) is used to find $b_{ij}$, the translation offset for the final transform.

B. Selection and Properties of the Imaging Zones

As part of the validation process, the user selects an imaging zone in the first imaging signal and an imaging zone in the second imaging signal. An imaging zone is the portion of an imaging signal selected to compare to another imaging signal (or another imaging zone in the same imaging signal). The selection of the imaging zones can occur in an automated way or it can rely upon user input. A variety of factors can be used to select an imaging zone, depending on the user's preferences, the contents of a biological sample, or the candidate imaging method and/or candidate imaging reagent.

An imaging zone can be selected so that it comprises areas of both signal and background. In some embodiments, the user can choose (manually or in an automated way) an imaging zone because it comprises the strongest signal from the biological sample or because it represents the background or lowest signal from the biological sample. On the other hand, an imaging zone can also be chosen randomly.

In some embodiments, an imaging zone contains at least 2, 3, 4, 5, 6, 7, 8, 9, 10, 11, 12, 13, 14, 15 or more elements (e.g., cells or distinct objects in the image). In some embodiments, the imaging zone is at least 2, 5, 10, 15, 20, 25, or 30 or more times the size of an average cell in the biological sample. In some embodiments, an imaging zone can comprise from tens to thousands of pixels in area, for example at least 10, 50, 100, 250, 500, 750, 1000, 2000, 3000, 5000 pixels or more. In some embodiments, an imaging zone can comprise all or nearly all of an image.

In some embodiments, only one imaging zone is compared between the first and second imaging signals. In some embodiments, at least one imaging zone in the first imaging signal is compared with the entire biological sample (or biological sample viewable in the image) in the second imaging signal. In some embodiments, two imaging zones are compared using this method. In some embodiments, more than two imaging zones are used. For example, in some embodiments, the method relies upon information from two or more imaging zones, for example 2, 3, 4, 5, 6, 7, 8, 9, 10, or more imaging zones.

C. Validating Candidate Imaging Methods or Candidate Imaging Reagents Through Cross-Correlation Cross-correlation is useful for quantitatively comparing a first imaging signal to a second imaging signal or to subsequent imaging signals in the case of multiple candidate imaging methods or candidate imaging reagents.

In signal processing, cross-correlation is a measure of similarity of two series as a function of the displacement of one relative to the other. This is also known as a sliding dot product or sliding inner-product. As an example, consider two real-valued functions $f$ (x,y) and g (x,y) differing only by an unknown shift along the x-axis and y-axis. One can use the cross-correlation to find how much g must be shifted along the x and y axes to make it identical to f. The process of cross-correlation essentially slides the g function along the x and y axes, calculating the integral of their product at each position. When the functions match, the value of the cross-correlation is maximized. This is because when peaks (positive areas) of one function are aligned with the other, they make a large contribution to the integral. When a peak in one function is not aligned with a peak in the other, the cross-correlation product will be much lower. In the case where f (x,y) and g (x,y) are not just copies of each other shifted by unknown offset, but where there are also differences between f and g which one wants to measure, the value of the maximum cross-correlation of f and g is a measure of the similarity of the two functions and the position of that maximum in x and y is the offset which produces the best match.

1. Cross-Correlating Imaging Zones to Validate the Candidate Imaging Method and Imaging Zone(s)

To perform the validation, one or more imaging zones (rectangular regions of interest) of Image A are selected for comparison with Image B (wherein Image A can be the first imaging signal and Image B can be the second imaging signal or vice versa). Validation can be performed with a single imaging zone, but for statistical robustness and to study possible spatial variability of the staining, multiple zones can be used. The size of each zone of Image A, in one embodiment, can be great enough in area to describe a unique signal pattern. For example, a small region around a single cell might easily match the image of many cells the other image, so image zones ideally include many to several hundred cells (tens to thousands of pixels in area). A zone can be as large as the entirety of an image to describe a global or overall likeness of Image A to Image B, or a zone could be a small fraction of Image A, in which case multiple non-overlapping zones could be selected at random, on a regular grid, or centered on features of interest (e.g., the brightest features) in order to study variability. For each zone of Image A, a corresponding zone of Image B is also selected. Due to the mathematics of convolution described below, the zones in Image B can ideally be larger (in both width and height) than the corresponding zones of Image A. At minimum, the zones of Image B can be larger than those in Image A by as many pixels as it takes to adequately sample the resolution of the two optical systems (i.e., the instrumental point spread function), but at a maximum they can be as large at the entirety of Image B. In some embodiments, the regions of Image A and the regions of Image B are the same dimensions, but in this case normalized cross-correlation might not be ideal. To test for a positive match, each zone of Image B should contain the same features of the slide in corresponding zone in Image A.

For each test zone, $Z_1$, centered at position (u, v) in Image A, Cross-Correlation image CC (u, v) of $Z_1$ with the corresponding zone, $Z_2$, of Image B is computed $$CC(u, v) = Z_2(x, y) * Z_1(u, v) = \sum_{x,y} Z_2(x, y) Z_1(x - u, y - v)$$

and also the Normalized-Cross-correlation image NCC (u, v):

$$NCC(u, v) = \frac{\sum_{x,y} \left[ [Z_2(x, y) - \overline{Z}_{2(u,v)}][Z_1(x - u, y - v) - \overline{Z}_1] \right]}{\left\{ \sum_{x,y} [Z_2(x, y) - \overline{Z}_{2(u,v)}]^2 \sum_{x,y} [Z_1(x - u, y - v) - \overline{Z}_1]^2 \right\}^{0.5}}$$

where $\overline{Z}_{2(u,v)}$ is the mean of $Z_2$ (x, y) over the zone $Z_1$ when it is at position (u, v), and $\overline{Z}_1$ is the mean of zone $Z_1$.

The CC(u, v) image can be thought of as a measure of the squared Euclidean distance between $Z_1$ and $Z_2$ at each offset (u, v). The peak pixel in CC(u, v) (i.e., the highest correlation value) represents the position with the greatest similarity of the two zones as well as the translational offset of that feature within CC(u, v) that is the best match of $Z_1$ to $Z_2$. The CC (u, v) peak value can have a wide range of values and will vary with the total image energy $\Sigma Z^2$ (x, y) in each zone and also with the size of features. A cross-correlation can be useful if Image A and Image B were captured with the same imaging modality (ideally with the same instrument) as it allows one to quantify brightness changes between the features of Image A and the features of Image B.

The NCC (u, v) image, on the other hand, is insensitive to differences in the overall brightness of $Z_1$ and $Z_2$ due to its normalization by $\overline{Z}_{2(u,v)}$ and $\overline{Z}_1$. This is especially useful if Image A and Image B are captured with different modalities and the intensity scale calibration between Image A and Image B is either unknown or uncertain. The peak in the NCC image can be thought of as a measure of the maximum similarly of the staining pattern of $Z_1$ with respect to $Z_2$, independent of the overall brightness and contrast of the two zones. Due to normalization, its value is constrained to be in the range from 0.0 to 1.0 inclusive. A NCC image peak value of 1.0 indicates and exact match, a value of 0.0 indicates anti-correlation. Thus, the NCC peak value can be used as a robust statistical measure of the similarity of the two imaging zones.

2. Additional Aspects of Cross-Correlation

In some embodiments, the step of identifying the first imaging zone in the second imaging signal in step (e) is the same as the cross-correlation step generating the peak cross-correlation in step (f) above. In some instances, the step of identifying the first imaging zone in the second imaging signal in step (e) is different from the cross-correlation step generating the peak cross-correlation in step (f) above.

In some embodiments, the cross-correlation is a normalized cross-correlation. In some embodiments, the normalized cross-correlation value is closer to 1 for a candidate imaging method or candidate imaging reagent that is validated, representing that the methods produce the same pattern in staining, considering both spatial layout and intensity. In some embodiments, the highest value from the normalized cross-correlation is at least 0.5, 0.6, 0.7, 0.75, 0.8, 0.85, 0.9, 0.91, 0.92, 0.93, 0.94, 0.95, 0.96. 0.97, 0.98, 0.99. In some embodiments the highest value from the normalized cross-correlation is 1.0. It can be especially useful to use the normalized cross-correlation when comparing different imaging methods where the imaging values can be on different scales. For example, two different imaging methods can be compared with a known, standard imaging method. If a first image obtained from a first candidate imaging method has the highest correlation value of 0.93 with the image obtained from the standard imaging method and a second image obtained from a second candidate imaging method has the highest correlation value of 0.90, the first image is a better match with the second image, indicating that the first imaging method provides a closer representation to the known, standard imaging method than the second imaging method. Based on this quantitative outcome of the cross-correlation values, one can decide on a threshold or tolerance level that constitutes a valid image. This threshold or tolerance level can be determined by applying the method described herein to a set of test images, ordering the images by the cross-correlation value or percent match value, inspecting the images in the order from a lower rank to determine the point at which the image becomes acceptable (or in a reversed order from a higher rank), and then selecting the cross-correlation value or percent match value of the image at that point as a threshold or tolerance level.

A user, however, does not need to normalize the cross-correlation in order to obtain useful information from the comparison. Thus, the cross-correlation can be unnormalized. In order to validate a candidate imaging method or candidate imaging reagent, the unnormalized cross-correlation would show a higher value. Whether normalized or not, a higher cross-correlation value represents a greater match between the staining patterns of the two images with respect to both the spatial distribution of the features in the imaging zones used and similarity of the intensities of those features. The unnormalized cross-correlation can be higher compared to a second imaging zone, compared to a different candidate imaging method or candidate imaging reagent (for example, candidate imaging method A and candidate imaging method B compared to each other), or it can be higher than a negative control or relatively high compared to a range between a negative control and a positive control (at least 50%, 60%, 70%, 80%, or 90% of the difference between the negative control and the positive control).

D. Method of Multiplexed Imaging and/or Exchange Imaging

New methods of performing multiplexed imaging and/or exchange imaging are available in the art. These methods, described in US Publication Nos. US20160319328 and US20180164308, which are incorporated herein by reference for their description of multiplexed imaging and exchange imaging throughout the applications, can optionally be used as one or more of the methods for comparison according to the methods herein. The present methods are useful for comparing between multiplexed imaging and/or exchange imaging reagents and/or methods, as well as between these methods and other imaging methods.

In some embodiments, the biological sample is contacted with at least two types of target-specific binding partners of different specificity. In some embodiments, in at least two target-specific binding partners of the same specificity are linked to different docking strands. In some embodiments, at least one nucleic acid strand linked to a target specific binding partner is a docking strand. In some embodiments, at least one nucleic acid strand linked to a target specific binding partner is a primer strand for amplification of docking strands. In some embodiments, the method includes amplification.

In some embodiments, the imager strands for the first imaging method are capable of binding a docking strand directly. In some embodiments, the imager strands for the first imaging method are capable of binding the docking strand indirectly. In some embodiments, the imager strands for the second imaging method are capable of binding a docking strand directly, while in others indirectly.

A variety of secondary imaging methods and reagents can be used as a basis for the comparison. In some situations, the second imaging method employs a secondary binding partner for the target-specific binding partner. In some instances, the secondary binding partner is added after the first imaging step. In some embodiments, the secondary binding partner is added after the target-specific binding partner, but before the first imaging step. In some embodiments, the secondary binding partner is added in a single staining step along with the target-specific binding partner.

A secondary binding partner can be a secondary antibody or antigen binding fragment thereof. A secondary binding partner can also be an aptamer, protein A, protein G, tertiary antibodies or antigen-binding fragments thereof, etc. Likewise, imager strands could also be labeled with fluorophores, haptens, small molecules, or proteins and a secondary binding partner could be a label-specific binding partner.

In some instances, the method includes removing the signal of the bound labeled imager strands from the docking strands after generating the first imaging signal. Removing the signal of the bound labeled imager strand can proceed in different ways: including by (i) inactivating the label (for example, photobleaching), (ii) by removing the label from the imager strand (for example, by cleaving a photocleavable linker attaching the label to the imager strand), or (iii) removing the bound labeled imager strands from the docking strands after generating the first imaging signal (by washing them away under appropriate conditions, by degrading or cleaving the imager strands so that they wash away, etc.).

In some embodiments, the labeled imager strands for the first imaging method comprise a fluorescent label. In some embodiments, at least one label is a fluorescent, enzymatic, or chromogenic label. In some embodiments, the method comprises at least one of fluorescence microscopy, brightfield microscopy, electron microscopy, or mass spectrometry imaging. In some embodiments, the labeled imager strands for the second imaging method comprise a fluorescent label.

Mass spectrometry imaging multiplexing can be performed using various heavy metal isotopes conjugated to antibodies for targets of interest. In such embodiments, the label can comprise a heavy metal isotope. Mass spectrometry, such as imaging mass cytometry and matrix assisted laser desorption/ionization imaging mass spectrometry (MALDI IMS), can be performed on tissue samples by ablating individual portions of a tissue sample and using mass spectrometry to determine if the heavy-metal isotope label is present in that individual portion of a tissue sample. See Giesen et al., Highly Multiplexed Imaging of Tumor Tissues with Subcellular Resolution by Mass Cytometry, Nature Methods 11(4):417-422 (2014); Norris et al., Imaging Mass Spectrometry: A New Tool for Pathology in a Molecular Age, Proteomics Clin Appl. 7(0):733-738 (2013).

E. Optionally Employing a Second or Subsequent Imaging Zone

In some modes, the method can comprise cross-correlating only the first imaging zone. In some modes, the method can comprise performing a cross-correlation on a second or subsequent imaging zone.

Thus, when a user desires to compare more than simply a first imaging zone across at least to imaging signals, the method can comprises identifying a second imaging zone in at least one of the first imaging signal and the second imaging signal. Comparing between two zones can provide an additional level of information as a user would not expect a high cross-correlation between a first imaging zone and a second imaging zone, whether within a single sample or different samples. This can be useful in many respects, but especially when a user relies on unnormalized cross-correlations.

A two zone method can further comprise comparing (i) the first imaging zone in the first imaging signal to the second imaging zone in the second imaging signal; (ii) the first imaging zone in the first imaging signal to the second imaging zone in the first imaging signal; (iii) the first imaging zone in the second imaging signal to the second imaging zone in the second imaging signal, by performing a cross-correlation and measuring the peak cross-correlation, wherein this cross-correlation serves as a negative control. More than one additional zone can be identified and cross-correlated as a negative control.

In some embodiments, the cross-correlation between the first imaging zone in the first imaging signal and the second imaging signal is higher than the negative control (at least 50%, 60%, 70%, 80%, or 90% of the difference between the negative control and the positive control).

II. Uses for this Method of Comparison

The present methods of comparison are useful for comparing different imaging methods and different reagents. The methods can be applied to validating an imaging method relative to another imaging method, or to test different imaging reagents in comparison to each other.

In some instances, the first imaging method or the first imaging reagent is the candidate imaging method or candidate imaging reagent. This is often, but not always, a fluorogenic method that relies on an imager strand bearing a fluorogenic label. In some instances, the second imaging method or the second imaging reagent is the candidate imaging method or candidate imaging reagent. This provides the capacity to evaluate a candidate imaging method or reagent that uses a secondary binding partner (such as an antibody or antigen binding part thereof) as part of the imaging process. The second imaging method or second imaging reagent, however, can also rely on an imager strand and can, optionally, include a fluorophore as its label. Thus, method can comprises contacting the biological sample with labeled imager strands for a second imaging method, wherein the labeled imager strands are capable of binding a docking strand, directly or indirectly.

The method can be used to compare two different imaging labels and/or imaging methods. In such a method, the first imaging reagent comprises a first label and a second imaging reagent comprising a second label. In some embodiments, the first label is one label from Table and wherein the second label is a different label from Table 1. In some embodiments, the first label is one of a fluorescent, enzymatic, or chromogenic label and wherein the second label is a different one of a fluorescent, enzymatic, or chromogenic label and wherein the second label.

TABLE 1

Labels for Imaging

| Chromogenic | Mass Tag (such as a Heavy Metal Isotope) |
|---|---|
| Contrast Agent | Metal or Metal-Based |
| Enzymatic | Metal-Organic Compound |
| Fluorescent | Nanoparticle |
| Isotope | Quantum Dot |
| Luminescent | Phosphorescent |
| Lanthanide | SERS |

In some embodiments, the labels being compared can each be one of the same group of labels. In some embodiments, one fluorescent label can be compared to another fluorescent label; one enzymatic label can be compared to another enzymatic label; or one chromogenic label compared to another chromogenic label, etc. for all of the label types in Table 1.

The two imaging methods can comprise different ones of fluorescence microscopy, brightfield microscopy, electron microscopy, mass spectrometry imaging, Raman imaging, surface enhanced Raman (SERs), atomic force microscopy (AFM), phase contrast imaging, X-ray tomography, multiphoton microscopy, scanning probe microscopy, infrared microscopy, or ultraviolet microscopy.

For example, the method can be used to compare a chromogenic imaging method with a fluorescent imaging method. Or it can be used to compare a chromogenic imaging method with a mass spectrometry imaging method.

In some embodiments, different docking strands can be compared to each other. In some embodiments, whether to use a primer strand can be evaluated. In such embodiments, one imaging method employs a primer strand and the other imaging method does not employ a primer strand. Likewise, a user can evaluate the impact of amplification. In some embodiments, one imaging method employs amplification and other imaging method does not employ amplification.

The impact of removing unbound target-specific binding partners can be evaluated. In such a situation, one imaging method removes unbound target-specific binding partners and the other imaging method does not remove unbound target-specific binding partners. The presence of unbound labeled imager strands can also be assessed. In such a method, one imaging method removes unbound labeled imager strands and the other imaging method does not remove unbound labeled imager strands.

In some embodiments, one imaging reagent includes a labeled imager strand capable of binding a docking strand indirectly and the other imaging reagent includes a labeled imager strand capable of binding a docking strand directly.

In some embodiments, the method of validating a candidate imaging method or candidate imaging reagent is for use in evaluating a biological sample for the presence of a single target. In some embodiments, the method of validating a candidate imaging method or candidate imaging reagent is for use in evaluating a biological sample for the presence of multiple targets.

Various forms of multiplexing or exchange imaging can be evaluated during this comparison. For example, multiplexing could be done at any staining step (before the first imaging method or after the first imaging method), with or without exchange. Exchange imaging could be done between the first imaging method and the second imaging method. Exchange could also be done within the first imaging method, and/or within the second imaging method.

Therefore, this technique provides a powerful tool for comparing and validating different imaging methods and reagents.

EXAMPLES

Example 1. Fluorescent Imaging of CD3

Fluorescent imaging of CD3 was conducted on a biological sample.

Formalin-fixed paraffin-embedded (FFPE) lung tissue was dewaxed and antigen-retrieved using a Lab Vision PT-module and pH 6 buffer. The tissue sample was blocked in a solution containing BSA and Triton-X 100 for 1.5 hours. Tissue was stained with a rabbit anti-CD3e primary antibody conjugated to docking strand D1 for 1 hour at room temperature in a humidity chamber. The tissue section was then washed with 1× PBS. A solution containing a circular DNA strand with complementarity to D1 was added to the sample and incubated for 25 minutes at room temperature. Following washing steps, amplification of the docking strands was carried out by applying a solution containing dNTPs and phi29 DNA Polymerase in 1× polymerase reaction buffer (New England Biolabs) and incubating for 2 hours at 30° C. The tissue was washed and DAPI was applied to stain nuclei.

A fluorescence microscope was used to image the tissue section in the DAPI and Cy5 channels to serve as a blank. An imager strand (I1), comprising a red fluorophore attached to DNA that includes a domain complementary to a docking strand D1, was added to the prepared tissue section and allowed to hybridize for 25 minutes at room temperature. Sections were washed to remove unbound I1. Then, fluorescence images were captured in the DAPI and Cy5 channels using a 20× objective and 10% Sola lamp power. Exposure times were at 100 ms for the DAPI channel and 500 ms for the Cy5 channel.

FIG. 1 provides a first imaging signal from a fluorescent stain of a biological sample.

Example 2. Chromogenic Brightfield Imaging of CD3

The same biological sample was used for chromogenic brightfield imaging of CD3.

Using the sample at the end of Example 1, the imager strand I1 was then removed by applying a solution of USER enzyme to the tissue section for 15 minutes at room temperature and washing with 1× PBS.

The tissue section was incubated with a peroxidase suppressor for 15 minutes at room temperature, washed, and incubated with a secondary antibody bound to horseradish peroxidase (HRP) for 1.5 hours. The tissue was washed and a mixture of 3,3'-diaminobenzidine (DAB) chromogen and substrate was added and allowed to incubate for 15 minutes, followed by a final washing step. Finally, the sample was imaged using brightfield illumination on an EVOS microscope with 10×, 20×, and 40× magnification FIG. 2 shows a second imaging signal from a chromogenic stain of the same biological sample as shown in FIG. 1.

Example 3. Comparing the Fluorescent Image and the Chromogenic Brightfield Image This example was created using a general-purpose computer (Mac Book Pro), with computer code written in C++ and the use of some functions from the open source image processing library OpenCV (opencv.org). The type of computer used, the choice of coding language and the use of the particular library are all optional: any practical computer could be used, the code could be written in another language, and the use of the library is not required.

Figure 2:
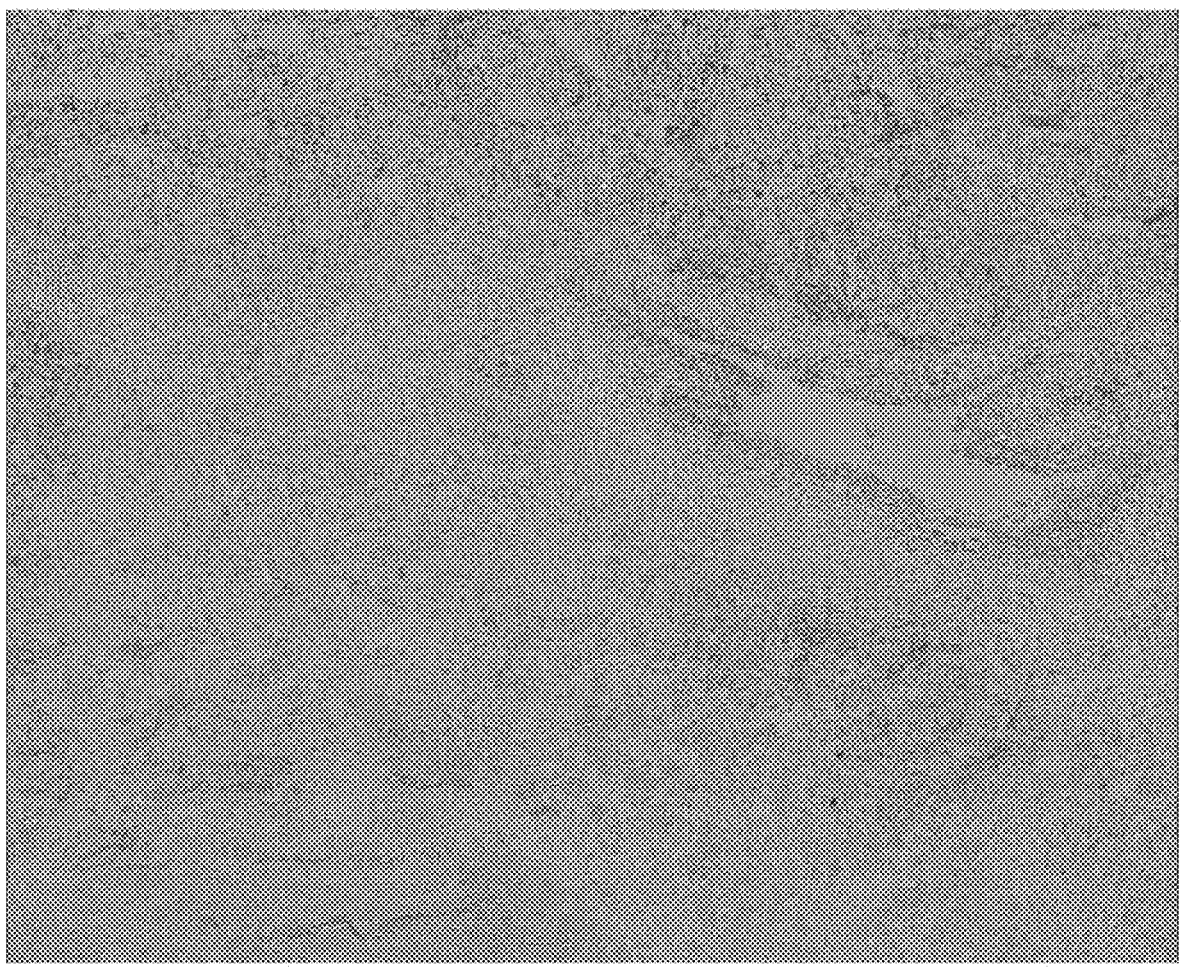
FIG. 2 shows a second imaging signal from a chromogenic stain of the same biological sample as shown in FIG. 1.
Figure 3:
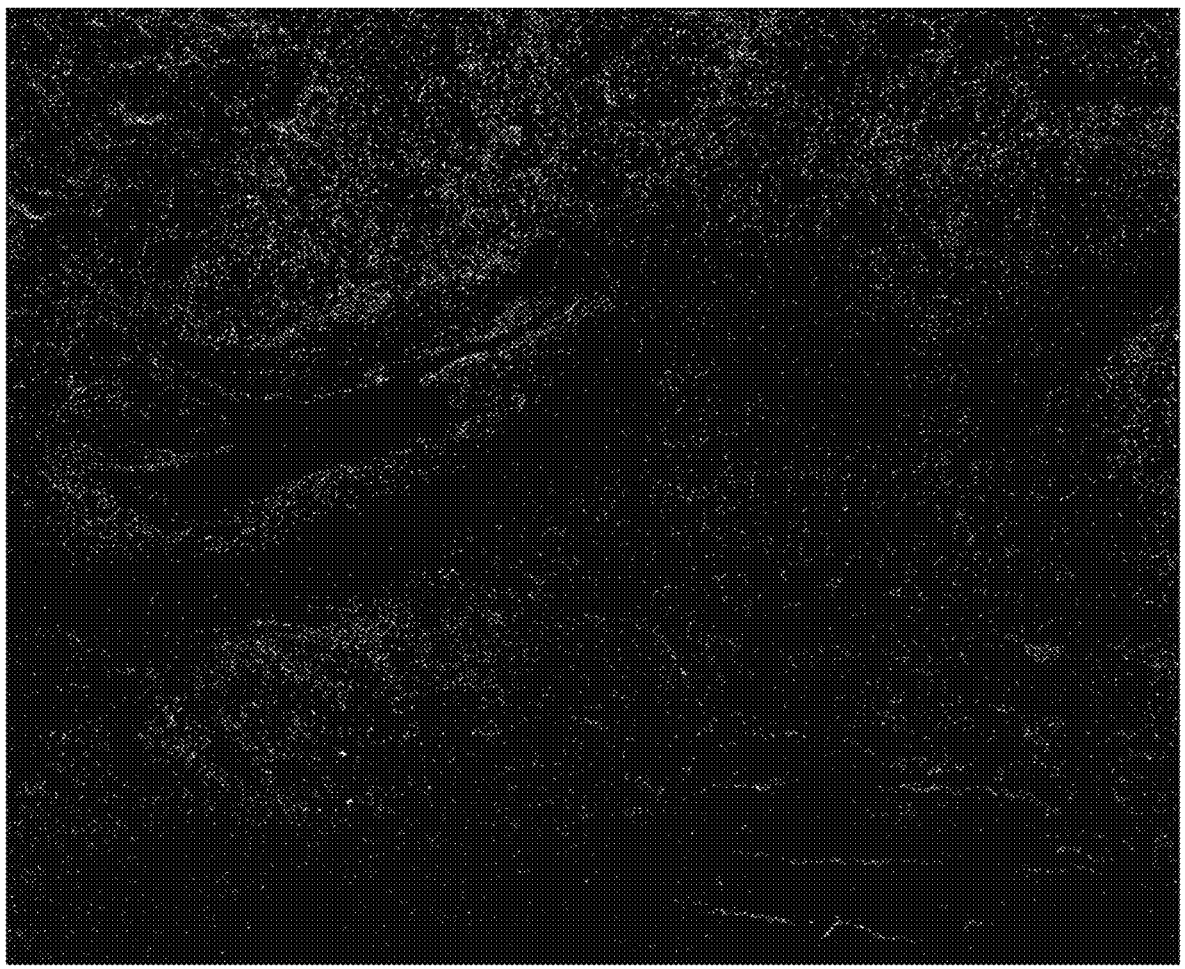
FIG. 3 shows the second imaging signal shown in FIG. 2 after image adjustments steps to align with the first imaging signal in FIG. 1.

The chromogenic brightfield image (3×8 bit RGB) of FIG. 2 underwent image processing steps to result in FIG. 3:
a. Converted the RGB image to HSV
b. Created a mask image selecting Hue values in the range 0 to 50°
c. Eroded the mask with a 2×2 rectangular kernel operator, one iteration.
d. Dilated the mask with a 3×3 cross (+) kernel operator, 8 iterations
e. Inverted the Value channel (255−V) and multiply by the mask
f. Found the minimum (0) and maximum values (238) and scale the intensities in this range to 0 to 255.
g. Calculated the Affine transform for a rotation of −0.331° about the center of the image, scaling the dimensions of the image by 1.36174.

$$\begin{bmatrix} 1.36173 & -0.0078668 & 33.1575 \\ 0.0078668 & 1.36172 & -40.4029 \\ 0 & 0 & 1 \end{bmatrix}$$

The scale factor and rotation angle, provided as inputs, were measured by the user by identifying corresponding features in the input images, and finding the ratio of the distance between them to determine the scale and finding the difference in their angle with respect to the x axis (arctangent) for the angle of rotation.

Thus, FIG. 3 shows the second imaging signal shown in FIG. 2 after image adjustments steps to align with the first imaging signal in FIG. 1.

A subsequent (optional) cropping step was performed match the bounds of the first imaging signal image to the bounds of the second imaging signal produced in the step above.
a. Calculated the normalized cross-correlation of the entire aligned second imaging signal image (FIG. 3) to the first imaging signal (FIG. 1).
b. Found the position of the peak (0.577) in the NCC image is at pixel position (677, 172)
c. Cropped the first imaging signal (FIG. 1) to a rectangle with top left corner at (677,172), width of 14020, and height of 11438 pixels (FIG. 4).

Figure 4:
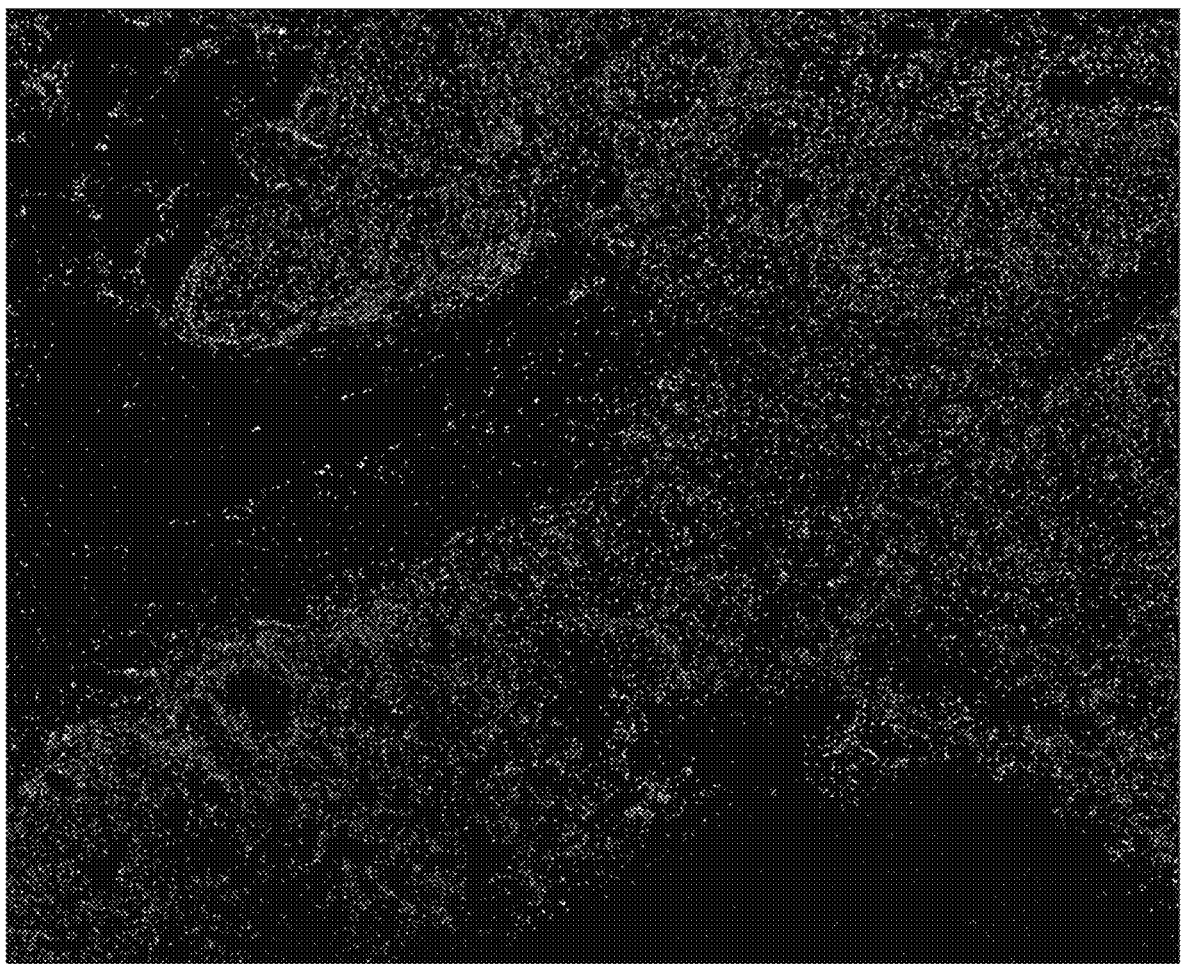
FIG. 4 shows the first imaging signal from FIG. 1 after optionally cropping the bounds of the first imaging signal to the bounds of the processed second imaging signal of FIG. 3.

Thus, FIG. 4 shows the first imaging signal from FIG. 1 after cropping to the bounds of the processed second imaging signal of FIG. 2.

Next, example imaging zones 1000 pixels wide and 1000 pixels high centered on signals of interest identified by the user were selected from the first imaging signal (FIG. 4) centered on signals of interest. The zones were expanded by 100 pixels on all 4 sides (width=1200, height=1200 pixels) for use as the corresponding imaging zones of the second imaging signal (FIG. 3).

Figure 5:
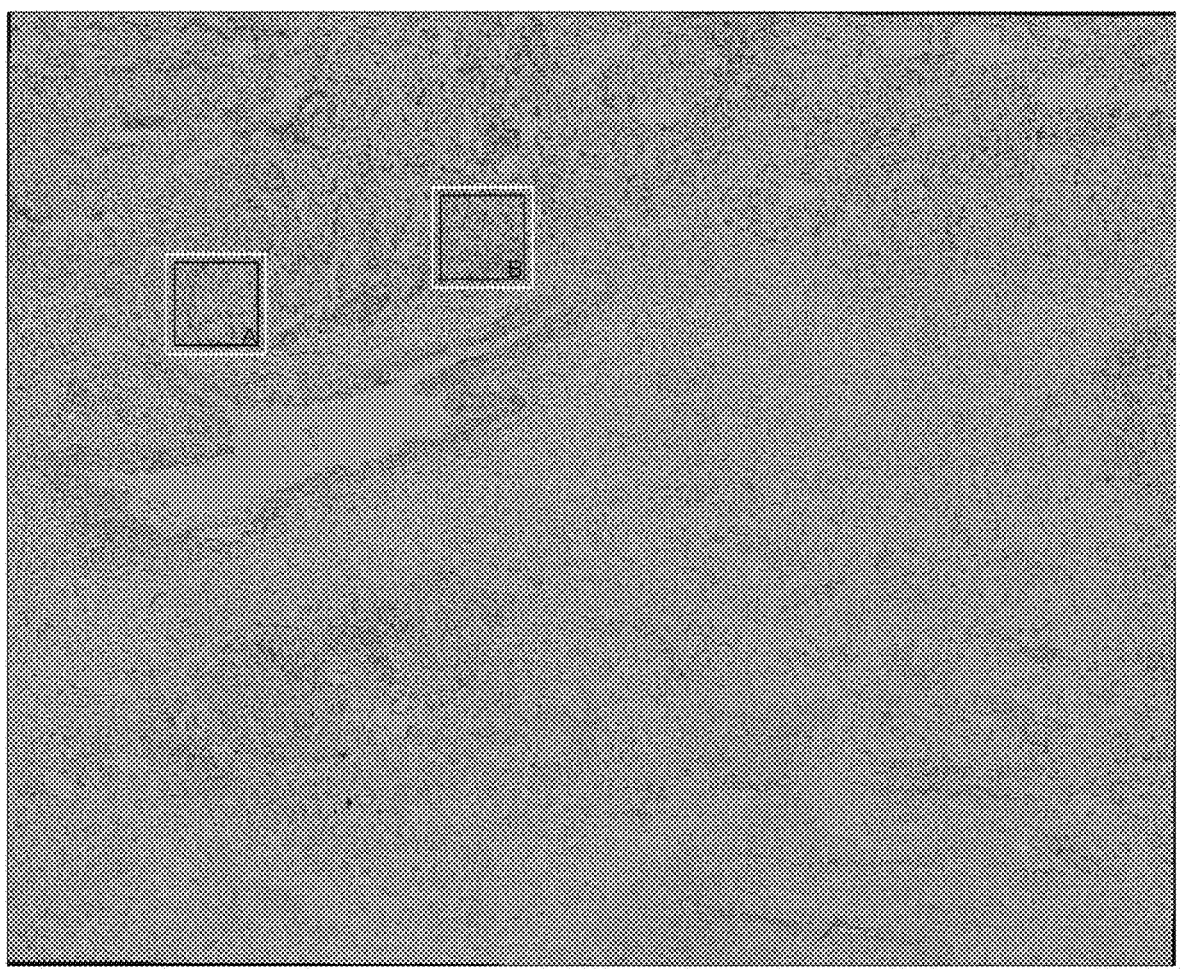
FIG. 5 shows an example first imaging zone (A) and an example second imaging zone (B) overlaid on the chromogenic stain of FIG. 2 after alignment. The black lines at A and B show the bounds of the example imaging zones in the first imaging signal (the fluorescent stain of FIG. 4) and the white lines at A and B show the bounds of the imaging zones in the second imaging signal (the chromogenic stain shown in FIG. 2 and FIG. 3).
Figure 7A:
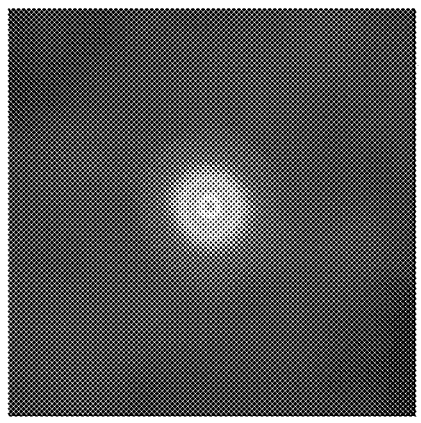
FIGS. 7A-D show the results of normalized cross-correlation images for different combinations of the example imaging zones A and B.
Figure 7B:
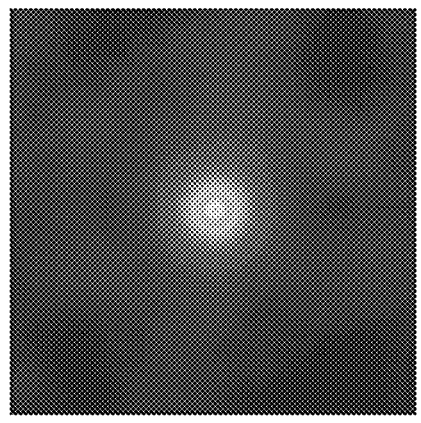
Figure 7C:
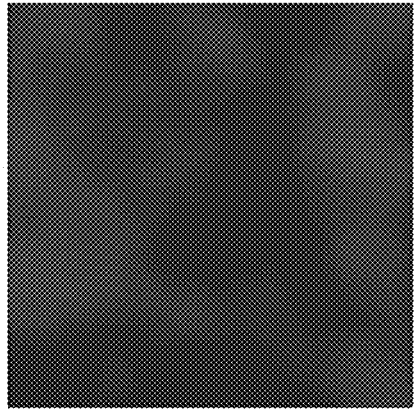
Figure 7D:
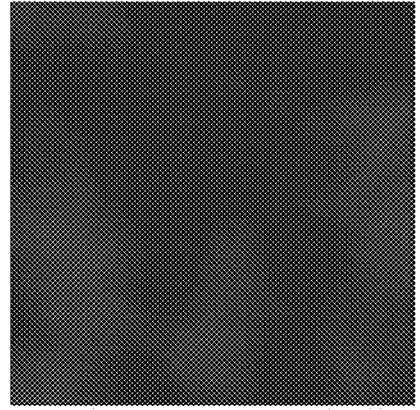

FIG. 5 shows a first example imaging zone (A) and a second example imaging zone (B) overlaid on a portion of the chromogenic stain of FIG. 2. The black lines at A and B show the bounds of the example imaging zones in the first imaging signal (fluorescent image) and white lines at A and B show the bounds of the example imaging zone in the second imaging signal (chromogenic stain).

FIGS. 6A-6D show details of the example imaging zones A and B in the aligned images of FIG. 3 and FIG. 4.

The normalized cross-correlation (NCC) image for all possible combinations of the example imaging zones from the first imaging signal with the example imaging zones of the second imaging signal was calculated. FIG. 7-D shows pseudo color representations where blue represents no correlation and red 100% correlation.

The peak value of each NCC image was found and is listed in Table 2. As expected, when the example imaging zone A from the fluorescent image was compared to the corresponding imaging zone A from the adjusted chromogenic image which contains the same staining pattern of the sample (positive test), the NCC image peak was quite high (>50%). On the other hand, when the same example imaging zone A from the fluorescent image was compared to the example imaging zone B from the adjusted chromogenic image which contains a different staining pattern (negative test), the NCC image peak was quite low (<10%).

TABLE 2

Normalized Cross-Correlation Values

| Correlation | NCC Image Peak |
|---|---|
| A vs. A | 0.728 |
| B vs. B | 0.682 |
| A vs. B | 0.057 |
| B vs. A | 0.048 |

This demonstrates that after first processing an image to align its signals with that of another image and then calculating the normalized cross-correlation of imaging zones of one with imaging zones of the other is an effective way to quantitatively compare the similarity of the signal pattern found in the different modalities.

Example 4. Additional Embodiments

The following numbered items provide additional support for and descriptions of the embodiments herein.

Item 1. A quantitative method of validating at least one candidate imaging method or candidate imaging reagent for use in evaluating a biological sample for the presence of one or more targets comprising:
  a. obtaining a first imaging signal using a first imaging method and/or first imaging reagents comprising:
    i. contacting a biological sample with one or more target-specific binding partners, wherein each target-specific binding partner is linked to a nucleic acid strand and wherein target-specific binding partners of different specificity, if present, are linked to different nucleic acid strands, wherein the nucleic acid strand is either a docking strand or a primer strand for amplification of docking strands;
    ii. contacting the biological sample with labeled imager strands for a first imaging method, wherein the labeled imager strands are capable of binding a docking strand, directly or indirectly,
    iii. generating a first imaging signal;
  b. optionally removing the bound labeled imager strands from the docking strands;
  c. obtaining a second imaging signal using a second imaging method and/or second imaging reagents comprising contacting the biological sample with either (1) labeled imager strands, wherein the labeled imager strands are capable of binding a docking strand, directly or indirectly, or (2) a secondary binding partner for the target-specific binding partner,
  wherein the second imaging method and/or the second imaging reagent is different the first imaging method and/or first imaging reagent;
  d. optionally aligning the first imaging signal and the second imaging signal to adjust for signal orientation, image parity, scale, rotation, and/or translation mismatch,
  e. identifying a first imaging zone in both the first imaging signal and second imaging signal, wherein the first imaging zone in both imaging signals represents the same location in the biological sample;
  f. comparing the first imaging zone in the first imaging signal and the first imaging zone in the second imaging signal by performing a cross-correlation.

Item 2. A quantitative method of validating at least one candidate imaging method or candidate imaging reagent for use in evaluating a biological sample for the presence of one or more targets comprising:
  a. obtaining a first imaging signal using a first imaging method and/or first imaging reagents,
  b. obtaining a second imaging signal using a second imaging method and/or second imaging reagents, wherein the second imaging method and/or the second imaging reagent is different the first imaging method and/or first imaging reagent;
  c. optionally aligning the first imaging signal and the second imaging signal to adjust for signal orientation, image parity, scale, rotation, and/or translation mismatch,
  d. identifying a first imaging zone in both the first imaging signal and second imaging signal, wherein the first imaging zone in both imaging signals represents the same location in the biological sample;
  e. comparing the first imaging zone in the first imaging signal and the first imaging zone in the second imaging signal by performing a cross-correlation.

Item 3. The method of items 1-2, wherein the cross-correlation comprises generating an image.

Item 4. The method of any one of items 1-3, wherein the cross-correlation comprises generating numerical data.

Item 5. The method of any one of items 1-4, wherein the cross-correlation comprises identifying the peak cross-correlation between the first imaging zone in the first imaging signal and the first imaging zone in the second imaging signal.

Item 6. The method of any one of items 1-5, wherein the cross-correlation comprises evaluating the breadth of the peak cross-correlation.

Item 7. The method of item 1, wherein the step of identifying the first imaging zone in the second imaging signal in step (e) is the same step as the cross-correlation step in step (f).

Item 8. The method of any one of items 1-7, wherein the cross-correlation is a normalized cross-correlation.

Item 9. The method of any one of items 1-8, wherein the normalized cross-correlation value is closer to 1 for a candidate imaging method or candidate imaging reagent that is validated.

Item 10. The method of any one of items 1-9, wherein the highest value from the normalized cross-correlation is at least 0.50.

Item 11. The method of any one of items 1-10, wherein the cross-correlation is unnormalized.

Item 12. The method of item 11, wherein the nonnormalized cross-correlation value is higher for a candidate imaging method or candidate imaging reagent that is validated.

Item 13. The method of any one of items 1-12, wherein the cross-correlation is computed in a spatial domain.

Item 14. The method of any one of items 1-13, wherein the cross-correlation is computed in a frequency domain.

Item 15. The method of any one of items 1-14, wherein the method comprises aligning the first imaging signal and the second imaging signal to adjust for signal orientation, image parity, scale, rotation, and/or translation mismatch.

Item 16. The method of item 15, wherein the method comprises aligning the first imaging signal and the second imaging signal to adjust for signal orientation.

Item 17. The method of any one of items 15-16, wherein the method comprises aligning the first imaging signal and the second imaging signal to adjust for image parity.

Item 18. The method of any one of items 15-17, wherein the method comprises aligning the first imaging signal and the second imaging signal to adjust for image scale.

Item 19. The method of any one of items 15-18, wherein the method comprises aligning the first imaging signal and the second imaging signal to adjust for image rotation.

Item 20. The method of any one of items 15-19, wherein the method comprises aligning the first imaging signal and the second imaging signal to adjust for translation mismatch.

Item 21. The method of any one of items 15-20, wherein the method further comprises intensity scaling.

Item 22. The method of any one of items 15-21, wherein the method further comprises morphology operations.

Item 23. The method of any one of items 1-22, wherein the biological sample is contacted with at least two types of target-specific binding partners of different specificity.

Item 24. The method of any one of items 1-23, wherein at least two target-specific binding partners of the same specificity are linked to different docking strands.

Item 25. The method of any one of items 1-24, wherein at least one nucleic acid strand linked to a target specific binding partner is a docking strand.

Item 26. The method of any one of items 1-25, wherein at least one nucleic acid strand linked to a target specific binding partner is a primer strand for amplification of docking strands.

Item 27. The method of any one of items 1-26, wherein method includes amplification.

Item 28. The method of any one of items 1-27, wherein the imager strands for the first imaging method are capable of binding a docking strand directly.

Item 29. The method of any one of items 1-28, wherein the imager strands for the first imaging method are capable of binding the docking strand indirectly.

Item 30. The method of any one of items 1-29, wherein the imager strands for the second imaging method are capable of binding a docking strand directly.

Item 31. The method of any one of items 1-30, wherein the imager strands for the second imaging method are capable of binding the docking strand indirectly.

Item 32. The method of any one of items 1-31, wherein the second imaging method employs a secondary binding partner for the target-specific binding partner.

Item 33. The method of item 32, wherein the secondary binding partner is added after the first imaging step.

Item 34. The method of items 33, wherein the secondary binding partner is added after the target-specific binding partner, but before the first imaging step.

Item 35. The method of any one of items 1-34, wherein the method includes removing the signal of the bound labeled imager strands from the docking strands after generating the first imaging signal.

Item 36. The method of any one of items 1-35, wherein removing the signal comprises inactivating the label.

Item 37. The method of any one of items 1-36, wherein removing the signal comprises removing the label from the imager strand.

Item 38. The method of any one of items 1-37, wherein removing the signal comprises removing the labeled imager strand from the docking strand.

Item 39. The method of any one of items 1-38, wherein the method does not include removing the signal of the bound labeled imager strands from the docking strands after generating the first imaging signal.

Item 40. The method of any one of items 1-39, wherein the labeled imager strands for the first imaging method comprise a fluorescent label.

Item 41. The method of any one of items 1-40, wherein at least one label is a fluorescent, enzymatic, or chromogenic label.

Item 42. The method of any one of items 1-41, wherein the method comprises at least one of fluorescence microscopy, brightfield microscopy, electron microscopy, or mass spectrometry imaging.

Item 43. The method of any one of items 1-42, wherein the labeled imager strands for the second imaging method comprise a fluorescent label.

Item 44. The method of any one of items 1-43, wherein the first imaging zone comprises the entire first imaging signal.

Item 45. The method of any one of items 1-44, wherein the second imaging zone comprises the entire second imaging signal.

Item 46. The method of any one of items 1-45, wherein the method compares two candidate imaging methods.

Item 47. The method of any one of items 1-46, wherein the method compares two candidate imaging reagents.

Item 48. The method of any one of items 1-47, wherein the method compares more than two candidate imaging methods.

Item 49. The method of any one of items 1-48, wherein the method compares more than two candidate imaging reagents.

Item 50. The method of any one of items 1-48, wherein the first imaging method or the first imaging reagent is the candidate imaging method or candidate imaging reagent.

Item 51. The method of any one of items 1-50, wherein the second imaging method or the second imaging reagent is the candidate imaging method or candidate imaging reagent.

Item 52. The method of any one of items 1-50, wherein the method comprises contacting the biological sample with labeled imager strands for a second imaging method, wherein the labeled imager strands are capable of binding a docking strand, directly or indirectly.

Item 53. The method of any one of items 1-52, wherein the method comprises contacting the biological sample with a secondary binding partner for the target-specific binding partner.

Item 54. The method of item 53, wherein the secondary binding partner for the target-specific binding partner is a secondary antibody or antigen-binding fragment thereof.

Item 55. The method of any one of items 1-54, wherein the method comprises comparing a first imaging reagent comprising a first label and a second imaging reagent comprising a second label.

Item 56. The method of item 55, wherein the first label is one of the labels in Table 1 and wherein the second label is a different one the labels in Table 1.

Item 57. The method of any one of items 1-56, wherein one imaging method comprises one fluorescence microscopy, brightfield microscopy, electron microscopy, mass spectrometry imaging, Raman imaging, surface enhanced Raman (SERs), atomic force microscopy (AFM), phase contrast imaging, X-ray tomography, multiphoton microscopy, scanning probe microscopy, infrared microscopy, or ultraviolet microscopy.

Item 58. The method of any one of items 1-57, wherein one imaging reagent comprises a first docking strand and the other imaging reagent comprises a second docking strand.

Item 59. The method of any one of items 1-58, wherein one imaging method employs a primer strand and the other imaging method does not employ a primer strand.

Item 60. The method of any one of items 1-59, wherein one imaging method employs amplification and the other imaging method does not employ amplification.

Item 61. The method of any one of items 1-60, wherein one imaging method removes unbound target-specific binding partners and the other imaging method does not remove unbound target-specific binding partners.

Item 62. The method of any one of items 1-61, wherein one imaging method removes unbound labeled imager strands and the other imaging method does not remove unbound labeled imager strands.

Item 63. The method of any one of items 1-62, wherein the first imaging reagent includes a labeled imager strand capable of binding a docking strand indirectly and the other imaging reagent includes a labeled imager strand capable of binding a docking strand directly.

Item 64. The method of any one of items 1-63, wherein the method of validating a candidate imaging method or candidate imaging reagent is for use in evaluating a biological sample for the presence of a single target.

Item 65. The method of any one of items 1-64, wherein the method of validating a candidate imaging method or candidate imaging reagent is for use in evaluating a biological sample for the presence of multiple targets.

Item 66. The method of any one of items 1-65, wherein the method further comprises identifying a second imaging zone in at least one of the first imaging signal and the second imaging signal.

Item 67. The method of item 66, wherein the method further comprises comparing
  a. the first imaging zone in the first imaging signal to the second imaging zone in the second imaging signal;
  b. the first imaging zone in the first imaging signal to the second imaging zone in the first imaging signal;
  c. the first imaging zone in the second imaging signal to the second imaging zone in the second imaging signal, by performing a cross-correlation and measuring the peak cross-correlation, wherein this cross-correlation serves as a negative control.

Item 68. The method of any one of items 66-67, wherein more than one additional zone is identified and cross-correlated as a negative control.

Item 69. The method of any one of items 66-68, wherein the cross-correlation is a unnormalized cross-correlation.

Item 70. The method of any one of items 66-69, wherein the cross-correlation between the first imaging zone in the first imaging signal and the second imaging signal is higher than the negative control (at least 50%, 60%, 70%, 80%, or 90% of the difference between the negative control and the positive control).

Item 71. The method of any one of items 1-70, wherein at least one imaging zone comprises areas of both signal and background.

Item 72. The method of any one of items 1-71, wherein at least one imaging zone contains at least 2, 3, 4, 5, 6, 7, 8, 9, 10, 11, 12, 13, 14, 15 imaging elements.

Item 73. The method of any one of items 1-72, wherein one imaging zone comprises the strongest signal from the biological sample in the first and/or second imaging signal.

Item 74. The method of any one of items 1-73, wherein an imaging zone is chosen because it comprises the strongest signal from the biological sample.

Item 75. The method of any one of items 1-74, wherein at least one imaging zone is chosen randomly.

Item 76. The method of any one of items 1-75, wherein at least one imaging zone is at least 5, 10, 15, 20, 25, or 30 times the size of an average cell in the biological sample.

Item 77. The method of any one of items 1-76, wherein the first imaging zone and the second imaging zone are non-overlapping.

Item 78. The method of any one of items 1-77, wherein at least one imaging zone in the first and second imaging signal comprise all of the same portions of the biological sample.

Item 79. The method of any one of items 1-78, wherein the first imaging zone in the first and second imaging signal comprise 90% of the same portions of the biological sample.

Item 80. The method of any one of items 1-79, wherein only one imaging zone is compared between the first and second imaging signals.

Item 81. The method of any one of items 1-80, wherein at least one imaging zone in the first imaging signal is compared with the entire biological sample in the second imaging signal.

Item 82. The method of any one of items 1-81, wherein more than two imaging zones are used.

Item 83. The method of any one of items 2-82, wherein the first imaging method employs a first targeting antibody bound directly or indirectly to a first label and the second imaging method employs a second targeting antibody bound directly or indirectly to a second label.

Item 84. The method of item 83, wherein the first targeting antibody is bound directly to a first label.

Item 85. The method of any one of items 83-84, wherein the second targeting antibody is bound directly to a second label.

EQUIVALENTS

The foregoing written specification is considered to be sufficient to enable one skilled in the art to practice the embodiments. The foregoing description and Examples detail certain embodiments and describe the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term "about" refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about can include numerical values that are rounded to the nearest significant figure.

What is claimed is:
1. A quantitative method of validating at least one candidate imaging method or candidate imaging reagent for use in evaluating a biological sample for the presence of one or more targets comprising:
  a. obtaining a first imaging signal using a first imaging method and/or first imaging reagents comprising:

i. contacting a biological sample with one or more target-specific binding partners, wherein each target-specific binding partner is linked to a nucleic acid strand and wherein target-specific binding partners of different specificity, if present, are linked to different nucleic acid strands, wherein the nucleic acid strand is either a docking strand or a primer strand for amplification of docking strands;
ii. contacting the biological sample with labeled imager strands for a first imaging method, wherein the labeled imager strands are capable of binding a docking strand, directly or indirectly,
iii. generating a first imaging signal;

b. optionally removing the bound labeled imager strands from the docking strands;

c. obtaining a second imaging signal using a second imaging method and/or second imaging reagents comprising contacting the biological sample with either (1) labeled imager strands, wherein the labeled imager strands are capable of binding a docking strand, directly or indirectly, or (2) a secondary binding partner for the target-specific binding partner,
wherein the second imaging method and/or the second imaging reagent is different from the first imaging method and/or first imaging reagent;

d. optionally aligning the first imaging signal and the second imaging signal to adjust for signal orientation, image parity, scale, rotation, and/or translation mismatch, e. identifying a first imaging zone in both the first imaging signal and second imaging signal, wherein the first imaging zone in both imaging signals represents the same location in the biological sample;

f. comparing the first imaging zone in the first imaging signal and the first imaging zone in the second imaging signal by performing a cross-correlation.

2. The method of claim 1, wherein the cross-correlation comprises generating an image.

3. The method of claim 1, wherein the cross-correlation comprises generating numerical data.

4. The method of claim 1, wherein the cross-correlation comprises identifying the peak cross-correlation between the first imaging zone in the first imaging signal and the first imaging zone in the second imaging signal.

5. The method of claim 1, wherein the cross-correlation comprises evaluating the breadth of the peak cross-correlation.

6. The method of claim 1, wherein the step of identifying the first imaging zone in the second imaging signal in step (e) is the same step as the cross-correlation step in step (f).

7. The method of claim 1, wherein the cross-correlation is a normalized cross-correlation.

8. The method of claim 7, wherein the normalized cross-correlation value is closer to 1 for a candidate imaging method or candidate imaging reagent that is validated.

9. The method of claim 7, wherein the highest value from the normalized cross-correlation is at least 0.50.

10. The method of claim 1, wherein the cross-correlation is unnormalized.

11. The method of claim 10, wherein the nonnormalized cross-correlation value is higher for a candidate imaging method or candidate imaging reagent that is validated.

12. The method of claim 1, wherein the cross-correlation is computed in a spatial domain.

13. The method of claim 1, wherein the cross-correlation is computed in a frequency domain.

14. The method of claim 1, wherein the method comprises aligning the first imaging signal and the second imaging signal to adjust for signal orientation, image parity, scale, rotation, and/or translation mismatch.

15. The method of claim 14, wherein the method comprises aligning the first imaging signal and the second imaging signal to adjust for signal orientation.

16. The method of claim 14, wherein the method comprises aligning the first imaging signal and the second imaging signal to adjust for image parity.

17. The method of claim 14, wherein the method comprises aligning the first imaging signal and the second imaging signal to adjust for image scale.

18. The method of claim 14, wherein the method comprises aligning the first imaging signal and the second imaging signal to adjust for image rotation.

19. The method of claim 14, wherein the method comprises aligning the first imaging signal and the second imaging signal to adjust for translation mismatch.

20. The method of claim 14, wherein the method further comprises intensity scaling.

21. The method of claim 14, wherein the method further comprises morphology operations.

22. The method of claim 1, wherein the biological sample is contacted with at least two types of target-specific binding partners of different specificity.

23. The method of claim 1, wherein the method includes removing the signal of the bound labeled imager strands from the docking strands after generating the first imaging signal.

24. The method of claim 1, wherein removing the signal comprises inactivating the label.

25. The method of claim 1, wherein at least one label is a fluorescent, enzymatic, or chromogenic label.

26. The method of claim 1, wherein the method comprises at least one of fluorescence microscopy, brightfield microscopy, electron microscopy, or mass spectrometry imaging.

27. The method of claim 1, wherein the method compares two candidate imaging methods.

28. The method of claim 1, wherein the method compares two candidate imaging reagents.

29. The method of claim 1, wherein the method comprises comparing a first imaging reagent comprising a first label and a second imaging reagent comprising a second label.

30. The method of claim 1, wherein one imaging method comprises one fluorescence microscopy, brightfield microscopy, electron microscopy, mass spectrometry imaging, Raman imaging, surface enhanced Raman (SERs), atomic force microscopy (AFM), phase contrast imaging, X-ray tomography, multiphoton microscopy, scanning probe microscopy, infrared microscopy, or ultraviolet microscopy.

31. The method of claim 1, wherein the method further comprises identifying a second imaging zone in at least one of the first imaging signal and the second imaging signal.

32. The method of claim 31, wherein the method further comprises comparing
 a. the first imaging zone in the first imaging signal to the second imaging zone in the second imaging signal;
 b. the first imaging zone in the first imaging signal to the second imaging zone in the first imaging signal;
 c. the first imaging zone in the second imaging signal to the second imaging zone in the second imaging signal,
by performing a cross-correlation and measuring the peak cross-correlation, wherein this cross-correlation serves as a negative control.

33. The method of claim 32 wherein more than one additional zone is identified and cross-correlated as a negative control.

34. The method of claim 32, wherein the cross-correlation is a unnormalized cross-correlation.

35. The method of claim 32, wherein the cross-correlation between the first imaging zone in the first imaging signal and the second imaging signal is higher than the negative control (at least 50%, 60%, 70%, 80%, or 90% of the difference between the negative control and the positive control).

36. The method of claim 1, wherein at least one imaging zone comprises areas of both signal and background.

37. The method of claim 1, wherein at least one imaging zone contains at least 2, 3, 4, 5, 6, 7, 8, 9, 10, 11, 12, 13, 14, 15 imaging elements.

38. The method of claim 1, wherein one imaging zone comprises the strongest signal from the biological sample in the first and/or second imaging signal.

39. The method of claim 1, wherein an imaging zone is chosen because it comprises the strongest signal from the biological sample.

40. The method of claim 1, wherein at least one imaging zone is chosen randomly.

41. The method of claim 1, wherein at least one imaging zone is at least 5, 10, 15, 20, 25, or 30 times the size of an average cell in the biological sample.

42. The method of claim 1, wherein the first imaging zone and the second imaging zone are non-overlapping.

43. The method of claim 1, wherein at least one imaging zone in the first and second imaging signal comprise all of the same portions of the biological sample.

44. The method of claim 1, wherein the first imaging zone in the first and second imaging signal comprise 90% of the same portions of the biological sample.

45. The method of claim 1, wherein only one imaging zone is compared between the first and second imaging signals.

46. The method of claim 1, wherein at least one imaging zone in the first imaging signal is compared with the entire biological sample in the second imaging signal.

47. The method of claim 1, wherein more than two imaging zones are used.

* * * * *